(12) United States Patent
Kurosaka

(10) Patent No.: US 8,696,124 B2
(45) Date of Patent: Apr. 15, 2014

(54) IMAGING APPARATUS AND OPHTHALMIC APPARATUS

(75) Inventor: Ryoji Kurosaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 80 days.

(21) Appl. No.: 13/230,067

(22) Filed: Sep. 12, 2011

(65) Prior Publication Data

US 2012/0099076 A1     Apr. 26, 2012

(30) Foreign Application Priority Data

Oct. 21, 2010   (JP) ................... 2010-236848

(51) Int. Cl.
*A61B 3/14* (2006.01)
*A61B 3/02* (2006.01)
*A61B 3/103* (2006.01)
*A61H 5/00* (2006.01)
*G02C 13/00* (2006.01)

(52) U.S. Cl.
CPC . *A61B 3/14* (2013.01); *A61B 3/103* (2013.01); *A61H 5/00* (2013.01); *G02C 13/005* (2013.01); *A61B 3/02* (2013.01)
USPC ........... 351/206; 351/200; 351/201; 351/204; 351/208; 351/209

(58) Field of Classification Search
USPC ................................ 351/200–209
See application file for complete search history.

(56) References Cited

U.S. PATENT DOCUMENTS

| 7,372,575 | B2 | 5/2008 | Fujita |
| 7,933,024 | B2 * | 4/2011 | Hirose ............ 356/497 |
| 7,982,881 | B2 * | 7/2011 | Fercher et al. .......... 356/497 |

| 2006/0146339 | A1 | 7/2006 | Fujita |
| 2010/0182567 | A1 | 7/2010 | Nouchi et al. |
| 2011/0267583 | A1 * | 11/2011 | Hayashi ............ 351/206 |

FOREIGN PATENT DOCUMENTS

| JP | 2006-162366 A | 6/2006 |
| JP | 2007-267927 A | 10/2007 |
| JP | 2008-289643 A | 12/2008 |
| WO | WO 2010079550 A1 * | 7/2010 |

OTHER PUBLICATIONS

M. Wojtkowski et al., Ultrahigh-resolution, high-speed, Fourier domain optical coherence tomography and methods for dispersion compensation, Optics Express, vol. 12, No. 11, May 31, 2004, pp. 2404-2422.

\* cited by examiner

*Primary Examiner* — Scott J Sugarman
*Assistant Examiner* — Daniele Manikeu
(74) *Attorney, Agent, or Firm* — Fitzpatrick, Cella, Harper & Scinto

(57) ABSTRACT

An imaging apparatus for obtaining a tomographic image of an object based on light obtained by combining returning light from the object, which is irradiated with measurement light, and reference light corresponding to that measurement light, the imaging apparatus comprising: a reference light splitting unit adapted to split the reference light into a plurality of reference light beams of different wavelength ranges, and a plurality of dispersion compensation units adapted to compensate dispersion in accordance with wavelength ranges of the plurality of reference light beams, the dispersion compensation units being provided in respective light paths of the plurality of reference light beams.

13 Claims, 8 Drawing Sheets

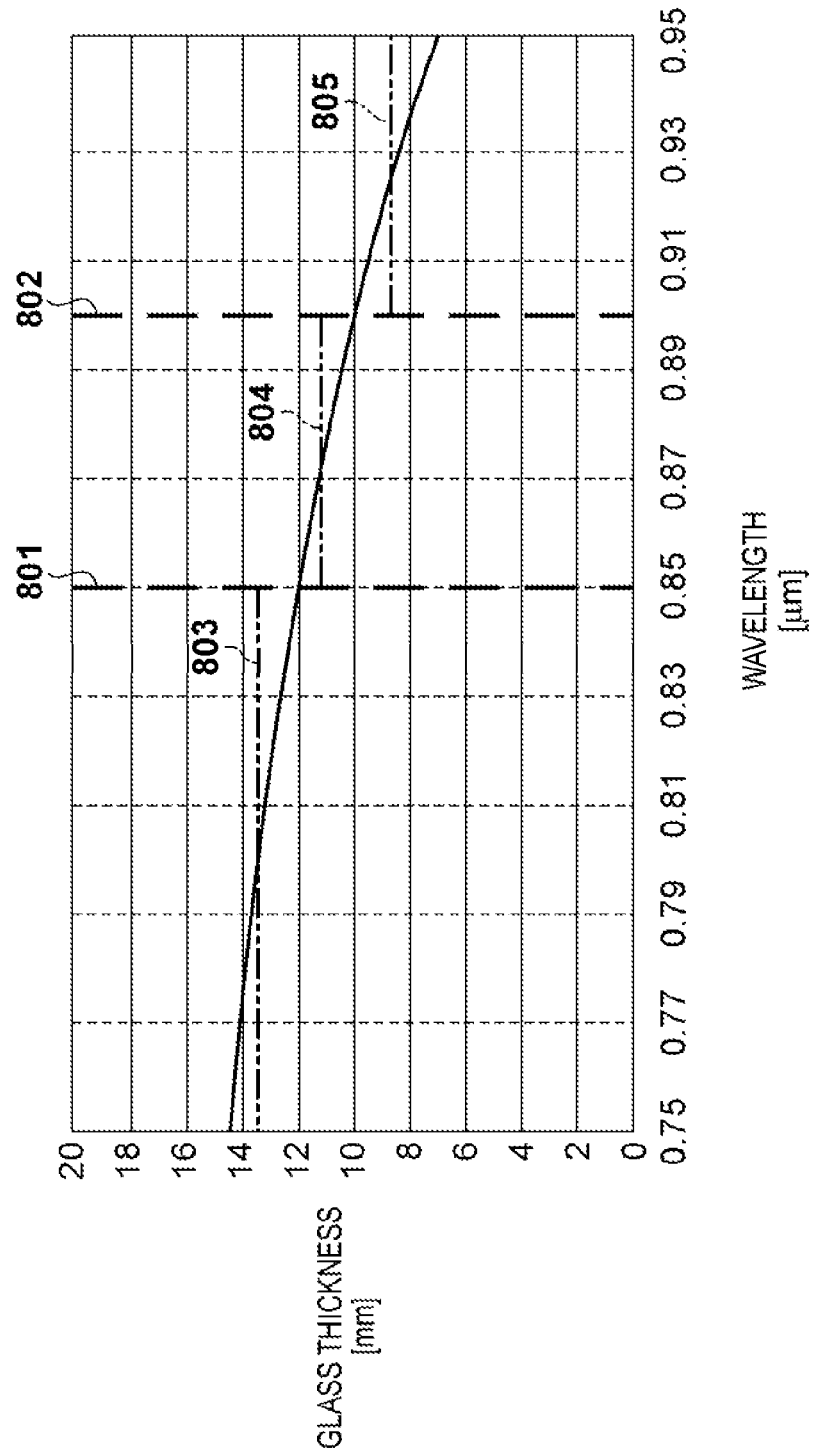

IMAGING APPARATUS AND OPHTHALMIC APPARATUS

BACKGROUND OF THE INVENTION

1. Field of the Invention

The present invention relates to an imaging apparatus and an ophthalmic apparatus, and more particularly relates to an imaging apparatus and an ophthalmic apparatus for tomographic imaging of a fundus or skin or the like using optical coherence tomography.

2. Description of the Related Art

In recent years, apparatuses for optical coherence tomography (referred to below as "OCT" below) using optical interference technology with low coherence light have been put into practice. OCT apparatuses are useful in the medical field, in particular in ophthalmology. They are apparatuses with which it is possible to obtain a tomographic image of the fundus/retina, and are becoming indispensable for the diagnosis of diseases of the fundus.

The following is a simple explanation of the principle of OCT. First, low coherence light is divided into reference light and measurement light. The measurement light is irradiated onto the measurement object, and by causing interference between the reference light and the returning light reflected from the tomographic imaging object region, it is possible to obtain a tomographic image of the measurement object. There are two OCT principles: TD (time domain) OCT and FD (fourier domain) OCT. In the FD-OCT method, the tomographic image is obtained by a Fourier transformation of the obtained interference signal. With this method, the tomographic image can be obtained faster than with the TD method, so that this method is presently the mainstream.

In recent years, there have been efforts to increase the resolution when obtaining the tomographic images in order to improve the image quality of the tomographic images. The resolution in OCT is classified into longitudinal resolution, which is the resolution in the optical axis direction of the measurement light, and lateral resolution, which is the resolution in a direction perpendicular to the optical axis direction. The resolution in longitudinal direction is important in order to identify the layer structure in fundus tomographic measurements using OCT, and the thickness of the layers is very important in judging eye diseases.

In OCT, the longitudinal resolution is determined mainly by the characteristics of the light that is used for the measurement. When the wavelength spectrum of the light has a Gaussian distribution, the longitudinal resolution can be expressed by the following equation:

[Eq. 1]

$$l_c = \frac{2\ln(2)}{\pi} \frac{\lambda_0^2}{\Delta\lambda} \quad (1)$$

Here, $l_c$ is the longitudinal resolution expressed as the full width at half-maximum of the coherence function. $\lambda_0$ represents the center wavelength of the light, and $\Delta\lambda$ represents the wavelength width of the light. In Equation (1), it is assumed that the wavelength spectrum has a Gaussian distribution. When light is used whose spectrum does not have a Gaussian distribution, then the longitudinal resolution will be poorer than expressed by (1), but since the center wavelength $\lambda_0$ and the wavelength width $\Delta\lambda$ undergo the same change, it does not lose its generality. With Equation (1), it can be seen that the longitudinal resolution can be improved by the two measures of:

(a) making the center wavelength $\lambda_0$ shorter, and
(b) widening the wavelength width $\Delta\lambda$ of the light. In OCT for ophthalmology, the infrared wavelength region (near 850 nm) is used. Due to optical absorption of visible light with the retina and absorption by the water in the vitreous body, there is a limit on the short-wavelength side. Consequently, since the wavelength range that can be used in ophthalmic OCT is limited on the short-wavelength side, it is difficult to increase the longitudinal resolution by making the center wavelength $\lambda$ shorter. Also, since it is necessary to avoid absorption losses by the vitrous body located in front of the fundus, in order to let the measurement light reach the fundus, there is also a limit on the long-wavelength side. Consequently, an increase of the longitudinal resolution is realized by (b) widening the wavelength width $\Delta\lambda$ of the light while giving consideration to these limits. Actually, since large-bandwidth low-coherence light is being put into practice in recent years, there is a discussion on improving the longitudinal resolution through (b) and its clinical merits (see for example "Ultrahigh-resolution, high-speed, Fourier domain optical coherence tomography and methods for dispersion compensation", OPTICS EXPRESS Vol. 12, No. 11, 31 May 2004, pp. 2404-2422). The following is a discussion on dispersion compensation. In OCT, it is necessary to match the dispersion characteristics between the reference light path and the measurement light path. This matching of the dispersion characteristics is called "dispersion compensation." FIG. 4 is a diagrammatic view showing an intensity profile in the depth direction by OCT for the case that dispersion compensation is performed and the case that dispersion compensation is not performed. The dotted line diagrammatically shows the profile that is obtained when no dispersion compensation is performed, whereas the solid line diagrammatically shows the profile when dispersion compensation is performed. FIG. 4 shows that when the dispersion compensation is insufficient, the intensity of the coherence function, which represents the resolution in the depth direction, drops, and the full width at half-maximum widens, so that the longitudinal resolution deteriorates.

Japanese Patent Laid-Open No. 2007-267927 discloses the use of water for dispersion compensation in OCT. A container that is filled with a medium of at least 70% water content is placed on the reference light path side. Through this medium, the characteristic feature is attained that the influence of the dispersion due to the measurement object can be suppressed.

Moreover, Japanese Patent Laid-Open No. 2006-162366 discloses an OCT apparatus having a plurality of light sources of different wavelength ranges, and splitting the reference light path in correspondence with the measurement light. By using a plurality of wavelength ranges, it is possible to obtain, at the same time, tomographic images of different depth regions.

In order to increase the longitudinal resolution using light of a large bandwidth in OCT, it is important to perform dispersion compensation across the entire used wavelength range. Since the dispersion characteristics of the measured object differ for each wavelength, there is the problem that the dispersion compensation becomes more difficult as the wavelength range becomes wider, and there is the risk that this impedes the improvement of the longitudinal resolution.

In "Ultrahigh-resolution, high-speed, Fourier domain optical coherence tomography and methods for dispersion compensation", OPTICS EXPRESS Vol. 12, No. 11, 31 May 2004, pp. 2404-2422, the dispersion compensation is performed with a plurality of glass materials for OCT using light of a large bandwidth. The dispersion characteristics of the materials water and glass differ greatly in the long wavelength region (the wavelength range of about 900 nm to 950 nm), so that there is the problem that it is difficult to perform the dispersion compensation with water over a large bandwidth.

In Japanese Patent Laid-Open No. 2007-267927, a dispersion compensation adapted to the OCT measurement object is carried out with water. However, with a dispersion compensation with water, there is the possibility that problems may occur in steady use with regard to temperature dependency and product quality.

Moreover, in Japanese Patent Laid-Open No. 2006-162366, it is possible to obtain, at the same time, tomographic images of different depth regions by using a plurality of wavelength ranges, but there is no dispersive material up to the region of interest of the tomographic images of the measured object, so that there is the problem that no consideration at all is given to dispersion compensation.

In view of the above problems, the present invention provides a technology for realizing dispersion compensation that is adapted to the dispersion characteristics of light of a large bandwidth.

SUMMARY OF THE INVENTION

According to one aspect of the present invention, there is provided an imaging apparatus for obtaining a tomographic image of an object based on light obtained by combining returning light from the object, which is irradiated with measurement light, and reference light corresponding to that measurement light, the imaging apparatus comprising: a reference light splitting unit adapted to split the reference light into a plurality of reference light beams of different wavelength ranges, and a plurality of dispersion compensation units adapted to compensate dispersion in accordance with wavelength ranges of the plurality of reference light beams, the dispersion compensation units being provided in respective light paths of the plurality of reference light beams.

According to one aspect of the present invention, there is provided an ophthalmic apparatus for obtaining a tomographic image of an eye to be examined based on light obtained by combining returning light from the eye to be examined, which is irradiated with measurement light, and reference light corresponding to that measurement light, the ophthalmic apparatus comprising: a reference light splitting unit adapted to split the reference light into a plurality of reference light beams of different wavelength ranges, and a plurality of dispersion compensation units adapted to compensate dispersion in accordance with wavelength ranges of the plurality of reference light beams, the dispersion compensation units being provided in respective light paths of the plurality of reference light beams.

Further features of the present invention will be apparent from the following description of exemplary embodiments with reference to the attached drawings.

BRIEF DESCRIPTION OF THE DRAWINGS

FIG. 8 is a graph showing wavelength splitting in accordance with the second embodiment.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
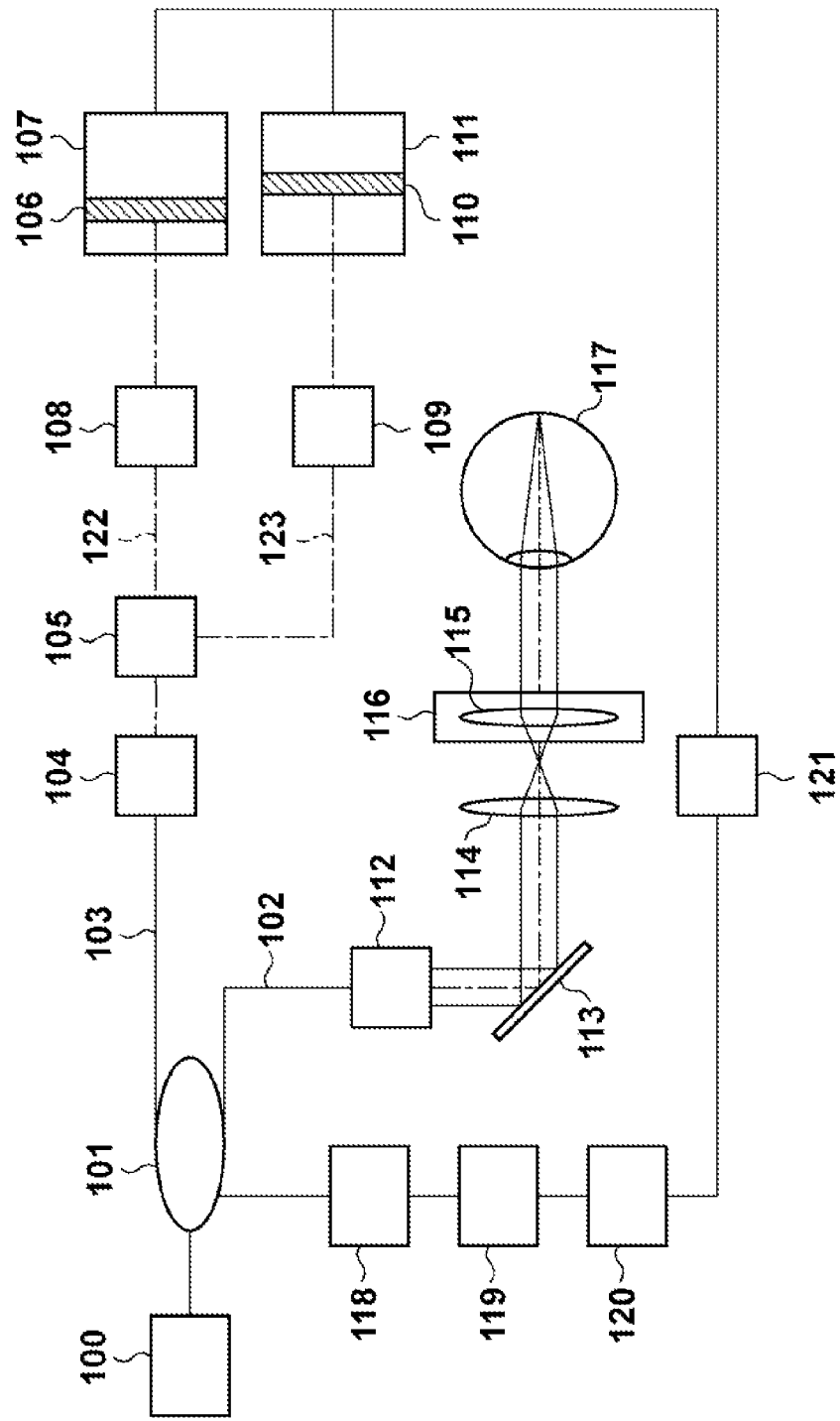
FIG. 1 is a diagram showing an optical coherence tomographic imaging apparatus according to a first embodiment.

First of all, an optical coherence tomographic imaging apparatus according to a first embodiment is explained with reference to FIG. 1. A light source 100 is for example an SLD (Super Luminsecent Diode) light source, but it may also be another type of light source, as long as it is a low coherent light source. More specifically, it may be a super-short pulse light source, such as an ASE (Amplified Spontaneous Emission) light source, a titanium sapphire laser or an SC (Super Continuum) light source, or an SS (Swept Source) light source.

A fiber coupler 101 splits light of a large bandwidth that is emitted from the light source 100 into reference light that passes through a fiber 103 constituting a reference light path, and measurement light that passes through a fiber 102 constituting a measurement light path. The splitting ratio at which the fiber coupler 101 splits the light into reference light and measurement light has a low wavelength dependency, and should be nearly constant. The split measurement light is emitted as parallel light from a fiber collimator 112. In order to scan over the retina of the eye 117 serving as the measurement object, the measurement light that has been turned into parallel light by passing through the fiber collimator 112 passes through a scanning optical system constituted by a scanner mirror 113 and a scanner lens 114, and is then focus-adjusted by an objective lens 115. After this, the measurement light is reflected by the retina of the eye 117, and travels along the above-described measurement light path in the opposite direction.

On the other hand, the reference light portion of the split light is emitted as parallel light from a fiber collimator 104, and irradiated onto a dichroic mirror 105. Then, the reference light is wavelength split by the dichroic mirror 105, and split into a plurality of reference light beams (reference light splitting process). More specifically, the short wavelength-side spectrum of the reference light irradiated from the light source 100 and split by the fiber coupler 101 passes through the reference light path 122, and the long wavelength-side spectrum passes through the reference light path 123. The reference light paths are respectively constituted by a dispersion compensation member 108 or a dispersion compensation member 109 that perform dispersion compensation, a reflection mirror 106 or a reflection mirror 110, and an electromotor stage 107 or an electromotor stage 111 that adjust the position of the reflection mirror. For the dispersion compensation member 108 and the dispersion compensation member 109, a material can be used that performs dispersion compensation with high precision in the wavelength range passing through the reference light paths 122 and the reference light path 123, respectively. More specifically, an optical glass, an optical plastic or the like may be used.

The position of the electromotor stage 107 and the electromotor stage 111 of the reference light paths is controlled by an electromotor stage controller 121. The electromotor stage controller 121 can independently or cooperatively adjust the position of the reflective mirror 106 and the reflective mirror 110 of the reference light paths. By arranging the electromotor stage 107 and the electromotor stage 111 in such a manner that they can independently adjust the positions of the reflective mirror 106 and the reflective mirror 110, it is possible to correct shifts in the light path lengths of the reference light path 122 and the reference light path 123, and to correct shifts in the longitudinal direction of the tomographic image that are caused by differences in the coherence gates of the interference signal between the short wavelength reference light and the measurement light, and the interference signal between the long wavelength reference light and the measurement light. Here, coherence gates refer to the position where the optical distance of the measurement light is the same as the optical distance of the reference light.

Figure 5:
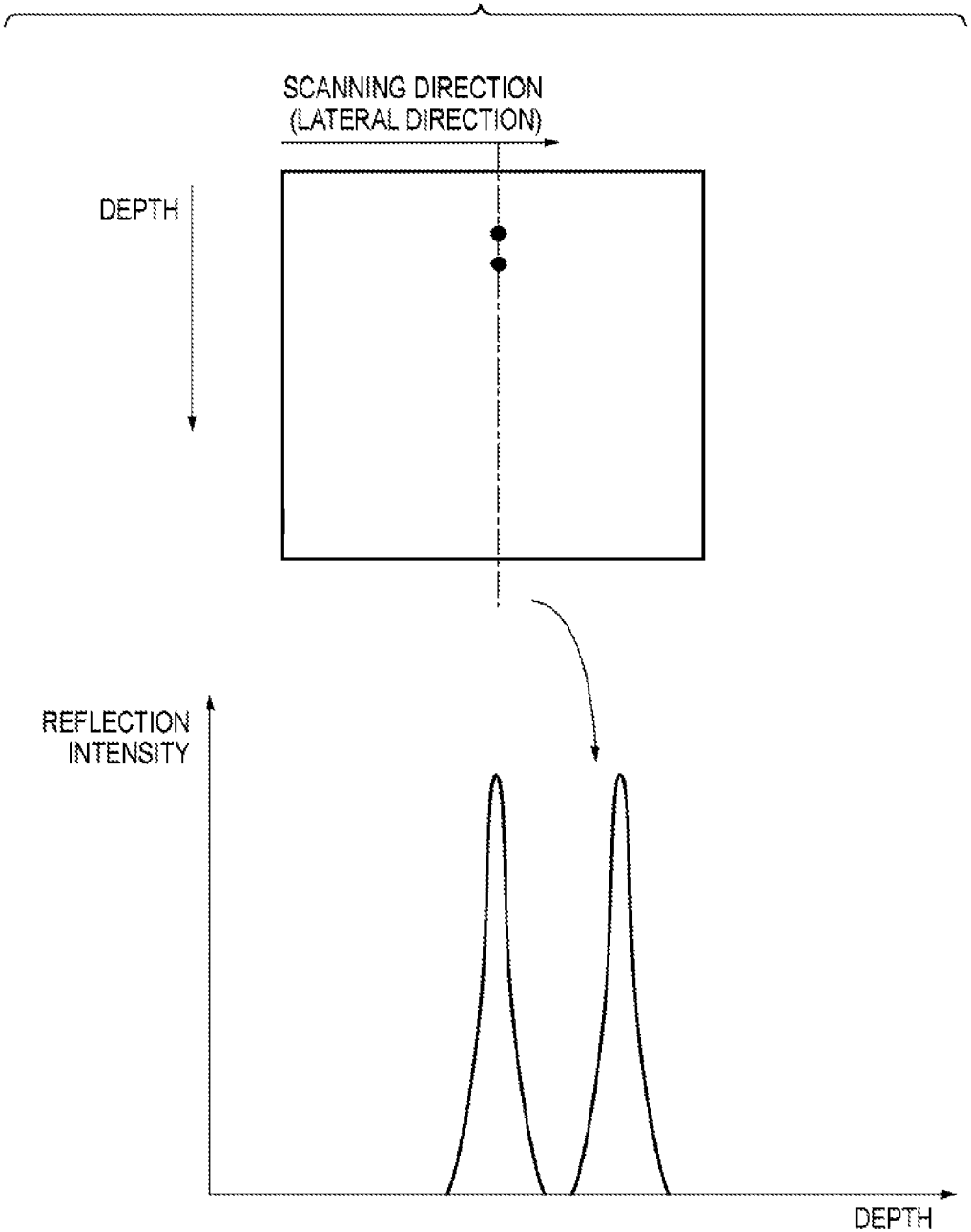
FIG. 5 is a diagram showing a tomographic image of a specular reflection mirror of a state in which there is a shift of the coherence gate according to the first embodiment.

The following is an explanation of the position shifts in the longitudinal direction of the coherence gates. Before measuring the eye 117, a specular reflection mirror is placed at the position of the eye 117 at the time of measurement, and the interference signal between the measurement light returning from the specular reflection mirror and the respective reference light is picked up with a camera, controlling the electromotor stage 107 and the electromotor stage 111 independently from each other. When, after this, a Fourier transformation is carried out, then there is a partition into two bright points in the tomographic image, as shown in FIG. 5. The reason for this is that since the dispersion compensation member 108 and the dispersion compensation member 109 in the respective reference light paths differ, the two coherence gates are located at separate positions on the electromotor stage 107 and the electromotor stage 111. Consequently, in a state using a specular reflective mirror, the above-noted bright points are caused to match by adjusting the electromotor stage 107 and the electromotor stage 111, and the relative positions of the electromotor stage 107 and the electromotor stage 111 at that time are stored in memory. Thus, it is possible to eliminate shifts in the tomographic images due to splitting of the reference light path. At this time, since a specular reflection mirror is used, there is nothing that corresponds to the portion of water in the eye 117, and the dispersion of the reference light path and the dispersion of the measurement light path do not match. However, when ascertaining the mutual relationship between the coherence gates in the reference light path 122 and the reference light path 123, it is not necessarily required to precisely match the dispersions. It should be noted that the dichroic mirror 105 performs wavelength splitting according to the wavelength dependency of reflection and transmission, but it is necessary to furthermore carry out a dispersion compensation for the portion of the wavelength range that passes through the dichroic mirror 105.

The reference light beams from the two reference light paths are combined by the dichroic mirror 105, and the returning measurement light is caused to interfere with the combined reference light at the fiber coupler 101, and after spectral division with a spectral divider 118, an interference signal is measured for each wavelength with a camera 119, and a tomographic image is obtained through analysis with a PC 120. The PC 120 is connected to the electromotor stage controller 121. By controlling the electromotor stage 107 and the electromotor stage 111 through the electromotor stage controller 121 with the PC 120, it is possible to adjust the electromotor stages to their optimal positions during the tomographic imaging of the eye 117.

The following is a more specific explanation of the dispersion compensation that is used on the measurement light path of the present embodiment. In the measurement light path, there are various types of lenses that are used for the measurement light path optical system, such as a scanner lens 114 and an objective lens 115, as well as the vitreous body and the crystalline lens of the eye 117 serving as the object to be measured, and their respective refractive indices are wavelength dependent. Consequently, it is necessary to insert members corresponding to these lenses, the vitreous body and the crystalline lens into the reference light path. The dispersion compensation of the various types of lenses can be accomplished by inserting the same lenses and is therefore not all that difficult. However, the vitreous body and the crystalline lens are constituted mainly by water, so that the dispersion compensation for the vitreous body and the crystalline lens is difficult.

Figure 3:
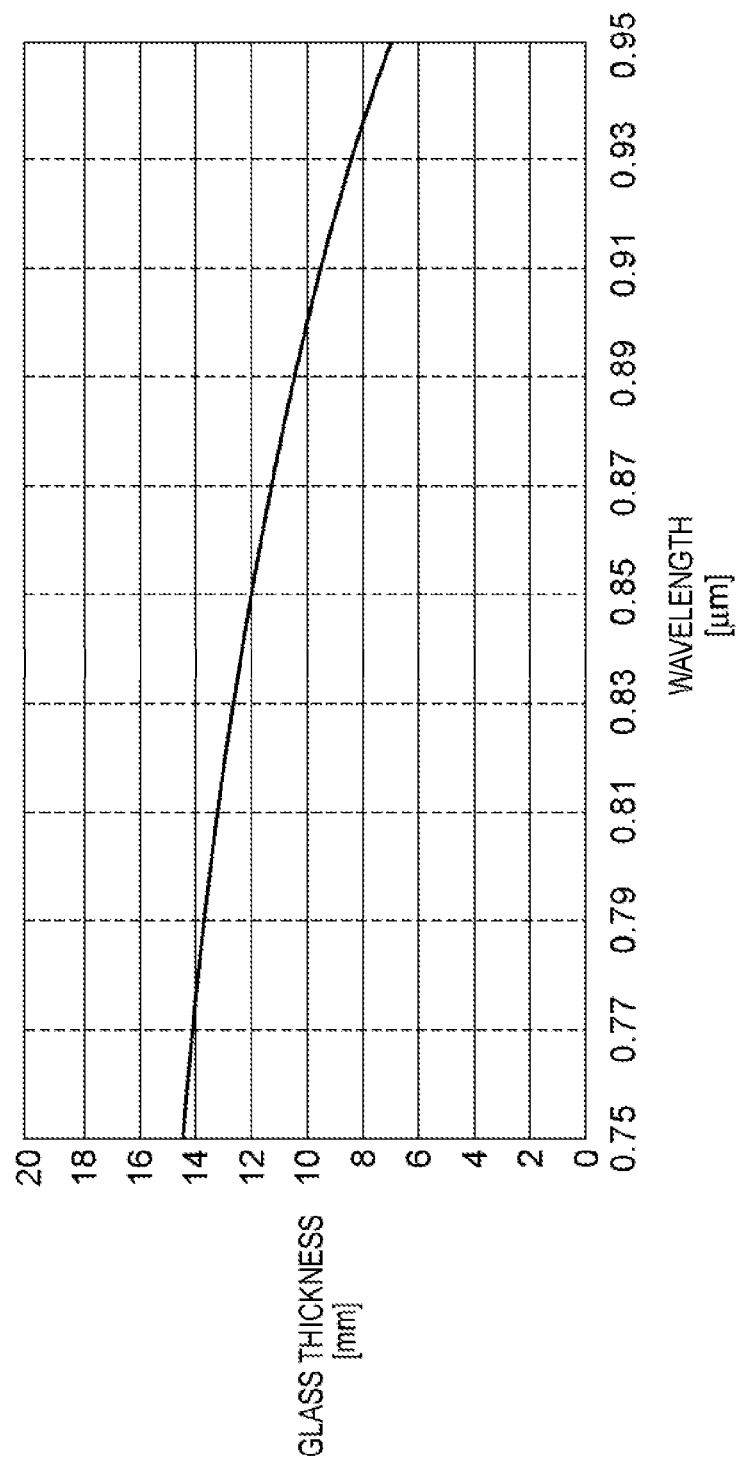
FIG. 3 is a graph showing an example of the wavelength dependency of the thickness of the glass, which is necessary for the dispersion compensation of water having a thickness that corresponds to the mean length of an eyeball.
Figure 4:
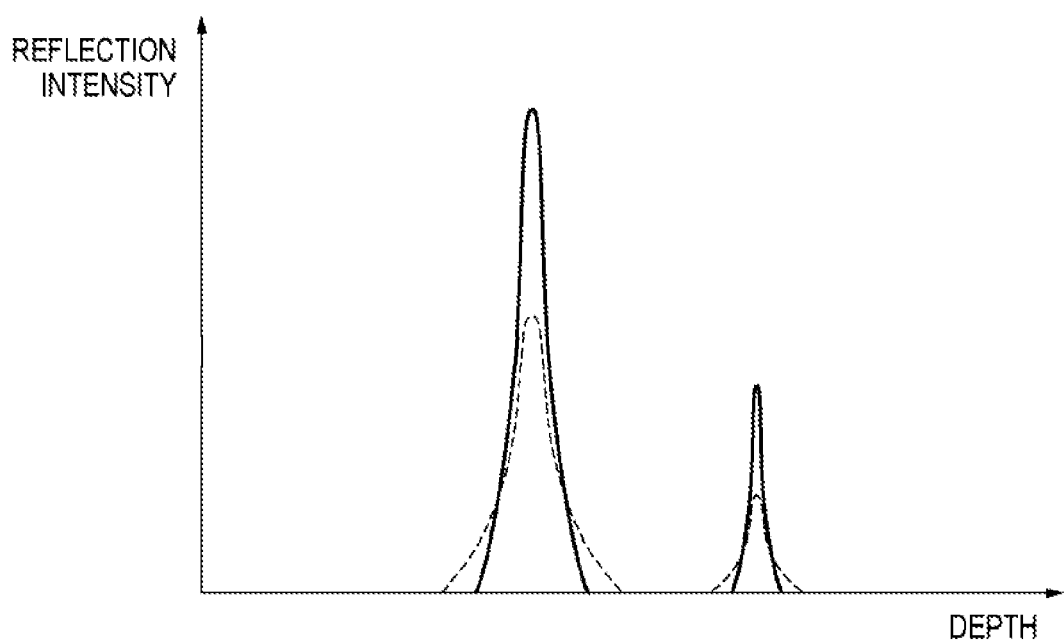
FIG. 4 is a graph that compares OCT intensity profiles with and without dispersion compensation.

FIG. 3 shows, as a function of wavelength, the thickness of ordinary optical glass that is necessary for dispersion compensation of a measured object having a mean eyeball length. As can be seen from FIG. 3, the glass thickness that is necessary for the dispersion compensation differs greatly between short wavelengths and long wavelengths. This is, because the dispersion characteristics of water are zero dispersion at a wavelength of about 1 µm, so that approaching 1 µm, the dispersion compensation becomes unnecessary.

The dispersion compensation members for the reference light paths are members that perform the dispersion compensation in the wavelength range passing through the reference light paths with high precision. For this, an even more precise dispersion compensation becomes possible by providing the feature of wavelength splitting. For the dispersion compensation member 108, a material is used that can perform dispersion compensation of water for short wavelengths with high precision, whereas for the dispersion compensation member 109, a material is used that can perform dispersion compensation of water for long wavelengths with high precision.

Figure 6A:
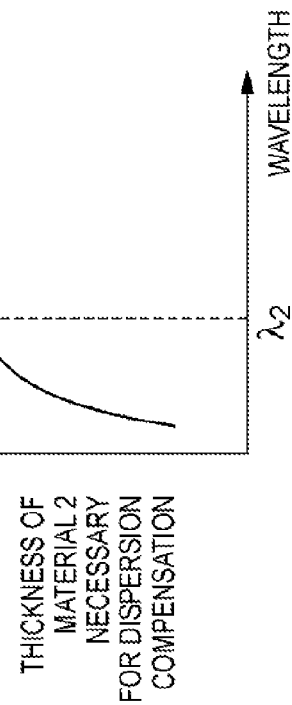
FIGS. 6A to 6D are diagrams showing reference light-path wavelength splitting in accordance with the first embodiment.
Figure 6B:
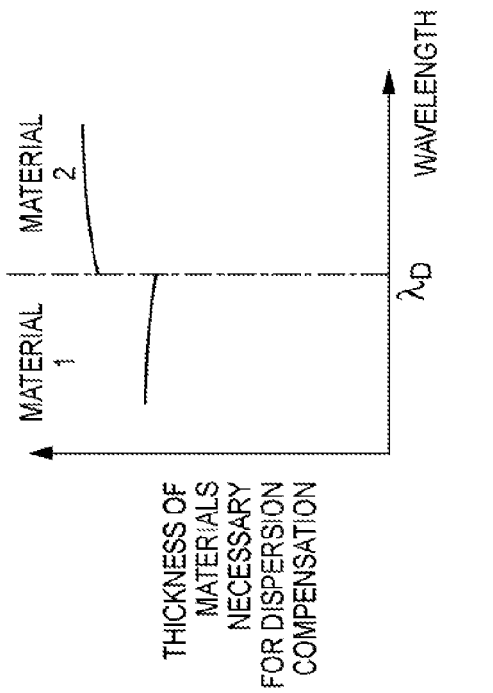
Figure 6C:
Figure 6D:
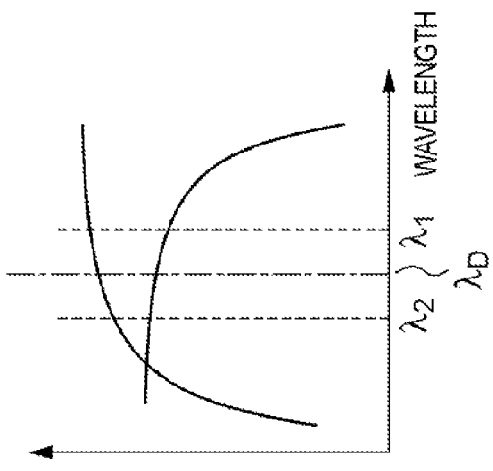

Referring to FIGS. 6A to 6D, the following is an explanation of the reference light path wavelength splitting. To measure the eye 117, a member of a material 1, with which dispersion compensation for short wavelengths can be performed with high precision, and a member of a material 2, with which dispersion compensation for long wavelengths can be performed with high precision, are used. FIG. 6A is a diagram showing the thickness of the material 1 that is necessary for the dispersion compensation as a function of the wavelength. For wavelengths that are smaller than $\lambda_1$, the dispersion compensation can be performed with high precision. The position of $\lambda_1$ may be set for example to the wavelength where the thickness is 90% of the thickness of the member of the material 1 for the shortest wavelength used. However, there is no limitation to 90%, and it may be set to any suitable value within a certain range. Moreover, the position of $\lambda_1$ may also be determined experimentally. FIG. 6B is a diagram showing the thickness of the material 2 that is necessary for the dispersion compensation as a function of the wavelength. FIG. 6C is a diagram showing the graphs of FIG. 6A and FIG. 6B overlapped with each other. FIG. 6D is a diagram in which the result of overlapping in FIG. 6C is reflected with $\lambda_D$ as the boundary.

The wavelength splitting is performed at a wavelength $\lambda_D$ that is intermediate between $\lambda_1$ and $\lambda_2$ at which the two members can carry out dispersion compensation with high precision. By using a member of the material 1 for the wavelength range $\lambda < \lambda_D$ and using a member of the material 2 for the wavelength range $\lambda > \lambda_D$, it is possible to perform dispersion compensation with high precision across the entire wavelength range. Here, $\lambda_1$ is a wavelength within the wavelength range where the wavelength dependency of the thickness of the material 1 that is necessary for dispersion compensation is relatively small, and in the present embodiment it is for example 0.85 μm. On the other hand, $\lambda_2$ is a wavelength within the wavelength range where the wavelength dependency of the thickness of the material 2 that is necessary for dispersion compensation is relatively small, and in the present embodiment it is for example 0.80 μm. Consequently, in the present embodiment, $\lambda_D$ is set to for example 0.83 μm.

Figure 7:
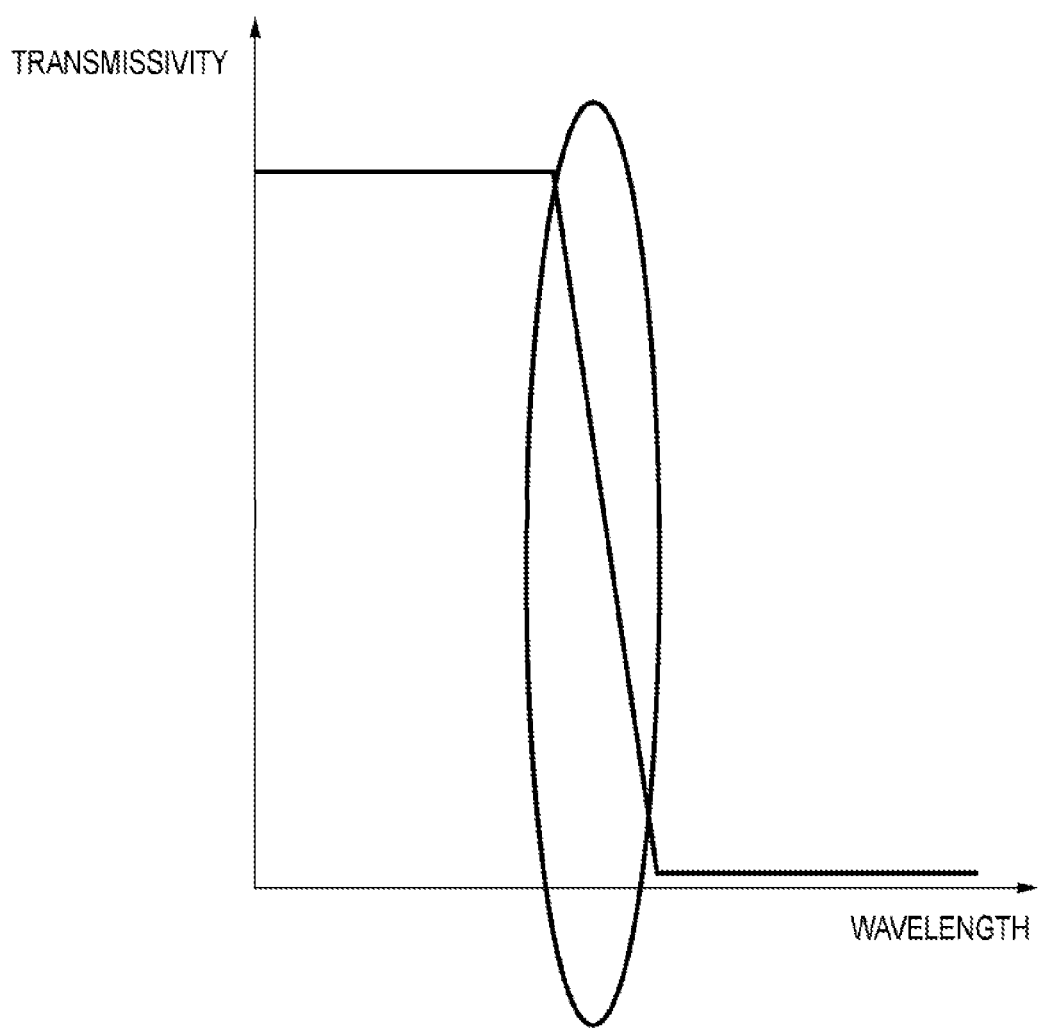
FIG. 7 is a diagram showing the transmissivity of a dichroic mirror as a function of wavelength.

Here, the wavelength splitting characteristics of the dichroic mirror 105 are as shown in FIG. 7. In the wavelength region that is enclosed by the ellipse in FIG. 7, the light is split into reference light that passes through both the reference light path 122 and the reference light path 123. This wavelength region is called "wavelength splitting region". It is preferable to match the dispersion of this wavelength splitting region in the reference light path 122 and the reference light path 123. In the present embodiment, the wavelength splitting region is set to the wavelength region near $\lambda_D$, as shown in FIGS. 6A to 6D. The wavelengths within the wavelength splitting region are subject to substantially the same dispersion, regardless of whether the light passes through the reference light path 122 or the reference light path 123. Consequently, even if there is a wavelength splitting region due to the dichroic mirror 105, the dispersion compensation can be carried out without problem.

With the present embodiment, it is possible to perform the dispersion compensation with high precision for each wavelength range. Moreover, it is possible to improve the longitudinal resolution through a highly precise dispersion compensation across a large bandwidth.

Second Embodiment

Figure 2:
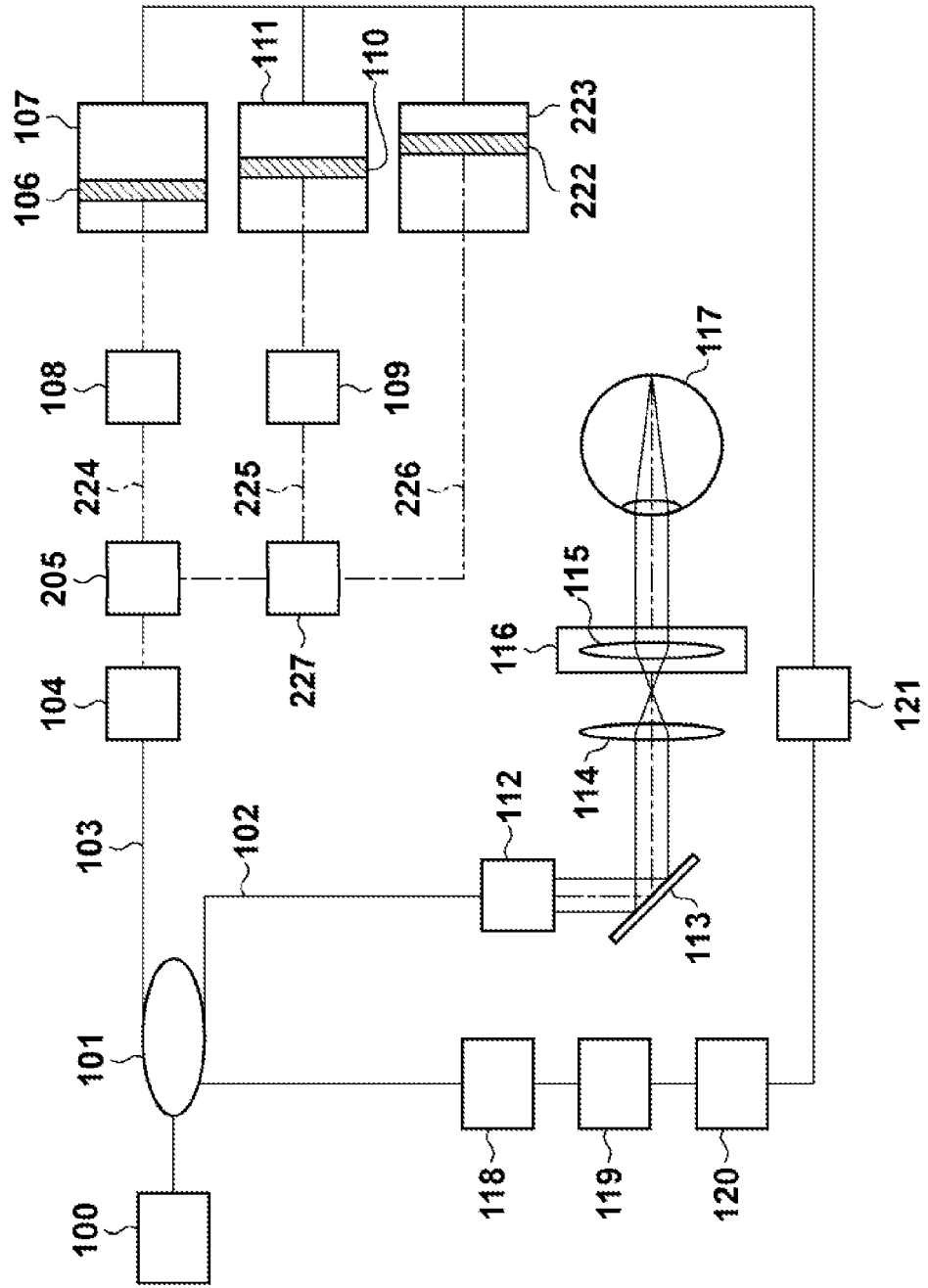
FIG. 2 is a diagram showing an optical coherence tomographic imaging apparatus according to a second embodiment.

Referring to FIG. 2, the following is an explanation of an optical coherence tomographic imaging apparatus according to a second embodiment. In this embodiment, dichroic mirrors perform wavelength splitting based on the wavelength dependency of the thickness of the dispersion compensation members introduced into the reference light path, that is necessary for the dispersion compensation of the measurement object.

More specifically, as shown in FIG. 3, the wavelength dependency of the dispersion compensation member thickness that is necessary for the dispersion compensation of the measurement object exhibits a large change on the long wavelength side. In the present embodiment, a more detailed dispersion compensation is performed by finer wavelength range splitting in the wavelength region in which there is a large change. As a result, the longitudinal resolution is improved even more.

More specifically, as shown in FIG. 2, three reference light paths are prepared, namely a reference light path 224, a reference light path 225, and a reference light path 226. It should be noted that the same reference numerals are given to elements that are the same as in FIG. 1, and their further explanation has been omitted. The reference light of the respective wavelength ranges that have been wavelength-split by the dichroic mirror 205 and the the dichroic mirror 227 passes respectively through the reference light path 224, the reference light path 225 and the reference light path 226. As shown in FIG. 2, the reference light of short wavelengths (not more than, for example, 850 nm), which is the range where the wavelength dependency of the thickness of the dispersion compensation member hardly changes at all, passes through the reference light path 224. Moreover, the reference light of the intermediate wavelength region, which is obtained by further splitting the reference light on the long wavelength side where the wavelength dependency of the thickness of the dispersion compensation member changes comparatively much, passes through the reference light path 225. And the reference light of the long wavelength region, which is obtained by further splitting the reference light on the long wavelength side where the wavelength dependency of the thickness of the dispersion compensation member changes comparatively much, passes through the reference light path 226. For the respective dispersion compensations of the reference light path 224, the reference light path 225 and the reference light path 226, the thicknesses of the dispersion compensation members should be suitable for the wavelength range of the reference light that respectively passes through them, and it is possible to achieve a dispersion compensation that is very precise, even when the thickness for the dispersion compensation of water changes considerably, as with ordinary glass material. It should be noted that the optical coherence imaging apparatus according to the second embodiment is further provided with a reflection mirror 222 and an electromotor stage 223 for adjusting the position of and the reflection mirror 222.

FIG. 8 illustrates the positions for the wavelength splitting in the present embodiment. On the short-wavelength side of the wavelength splitting position 801, there is hardly any change to the glass thickness that is necessary for the dispersion compensation. On the other hand, it can be seen that the glass thickness that is necessary for the dispersion compensation has a large wavelength dependency on the long wavelength side of the wavelength splitting position 801. Consequently, the wavelength range on the long wavelength side of the wavelength splitting position 801 is further split at the wavelength splitting position 802. The reference light with shorter wavelengths than the wavelength splitting position 801, the reference light of wavelengths between the wavelength splitting position 801 and the wavelength splitting position 802, and the reference light with longer wavelengths than the wavelength splitting position 802 passes through the respective reference light paths. The dispersion compensation should be set to the dispersion compensation amount that is necessary for the respective wavelength range, and more specifically to a glass thickness 803, a glass thickness 804 and a glass thickness 805 that is necessary for the dispersion compensation at substantially the center wavelength (for example, the mean wavelength of the wavelength range) of the various wavelength ranges as a representative wavelength. It should be noted that the position adjustment of the coherence gates is similar to that of the first embodiment, so that further explanations thereof are omitted.

With the present embodiment, it is possible to realize a dispersion compensation with high precision through wavelength splitting based on the wavelength dependency of the thickness of the dispersion compensation member. Moreover, it is possible to improve the longitudinal resolution of the obtained tomographic images.

With the present invention, it is possible to realize a dispersion compensation that addresses the dispersion characteristics of light of a large bandwidth.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-236848, filed on Oct. 21, 2010, which is hereby incorporated by reference herein in its entirety.

What is claimed is:

1. An imaging apparatus for obtaining a tomographic image of an object based on light obtained by combining (a) returning light from the object, which is irradiated with measurement light, and (b) reference light corresponding to that measurement light, the imaging apparatus comprising:
    a reference light splitting unit adapted to split the reference light into a plurality of reference light beams, the plurality of reference light beams having wavelength ranges different from each other; and
    a plurality of dispersion compensation units adapted to compensate dispersion in accordance with wavelength ranges of the plurality of reference light beams, each of the dispersion compensation units corresponding to a respective one of the wavelength ranges and being provided in a respective light path of light paths of the plurality of reference light beams.

2. The imaging apparatus according to claim 1, wherein the plurality of dispersion compensation units are a plurality of dispersion compensation members that each have a thickness that corresponds to a predetermined wavelength that is included in the wavelength range of the plurality of reference light beams.

3. The imaging apparatus according to claim 2, wherein the predetermined wavelength is a mean wavelength of the wavelength range.

4. The imaging apparatus according to claim 1, wherein the reference light splitting unit splits the reference light into a plurality of reference light beams, in accordance with wavelength ranges corresponding to dispersion characteristics of the object.

5. The imaging apparatus according to claim 1, wherein the reference light splitting unit is a dichroic mirror.

6. The imaging apparatus according to claim 1, further comprising an adjustment unit adapted to adjust the respective light path lengths of the plurality of reference light beams.

7. The imaging apparatus according to claim 1, wherein each of the plurality of dispersion compensation units is arranged between the reference light splitting unit and a reference object which reflects reference light and which is arranged at a respective light path of light paths of the plurality of reference light beams.

8. The imaging apparatus according to claim 1, wherein each of the plurality of reference light beams generated by the reference light splitting unit go through each of the plurality of dispersion compensation units, respectvely.

9. The imaging apparatus according to claim 1, wherein the plurality of dispersion compensation units are made of glass or plastic.

10. The imaging apparatus according to claim 1, wherein each of the thicknesses of the plurality of dispersion compensation units is different from each other.

11. An ophthalmic apparatus for obtaining a tomographic image of an eye to be examined based on light obtained by combining (a) returning light from the eye to be examined, which is irradiated with measurement light, and (b) reference light corresponding to that measurement light, the ophthalmic apparatus comprising:
    a reference light splitting unit adapted to split the reference light into a plurality of reference light beams, the plurality of reference light beams having wavelength ranges different from each other; and
    a plurality of dispersion compensation units adapted to compensate dispersion in accordance with wavelength ranges of the plurality of reference light beams, each of the dispersion compensation units corresponding to a respective one of the wavelength ranges and being provided in a respective light path of light paths of the plurality of reference light beams.

12. A compensation method comprising the steps of:
    splitting a light from a light source into reference light and measurement light;
    splitting the reference light into a plurality of reference light beams, the plurality of reference light beams having wavelength ranges different from each other;
    performing a dispersion compensation for each of the plurality of reference light beams using dispersion compensation units each corresponding to a respective one of the wavelength ranges of the reference light beams; and
    combining each dispersion-compensated reference light beam and returning light from an eye to be examined to which the measurement light is irradiated.

13. A non-transitory computer-readable storage medium storing a computer program for causing a computer to execute each step in a compensation method according to claim 12.

* * * * *